(12) United States Patent
Smith et al.

(10) Patent No.: US 10,878,962 B2
(45) Date of Patent: Dec. 29, 2020

(54) SYSTEM AND METHOD FOR EXTRACTING ONCOLOGICAL INFORMATION OF PROGNOSTIC SIGNIFICANCE FROM NATURAL LANGUAGE

(71) Applicant: Cota Inc., New York, NY (US)

(72) Inventors: Stephen August Smith, New York, NY (US); Dilip Raj, New York, NY (US); Ali Hasan, Great Neck, NY (US); Idan Waisman, New York, NY (US); Cory Parent, New York, NY (US)

(73) Assignee: COTA, Inc., New York, NY (US)

( * ) Notice: Subject to any disclaimer, the term of this patent is extended or adjusted under 35 U.S.C. 154(b) by 0 days.

(21) Appl. No.: 15/341,847

(22) Filed: Nov. 2, 2016

(65) Prior Publication Data
US 2018/0121618 A1     May 3, 2018

(51) Int. Cl.
| | | |
|---|---|---|
| *G16H 50/20* | (2018.01) | |
| *G16H 10/60* | (2018.01) | |
| *G16H 70/20* | (2018.01) | |
| *G16H 15/00* | (2018.01) | |
| *G06F 40/242* | (2020.01) | |
| *G06F 40/30* | (2020.01) | |
| *G06F 40/211* | (2020.01) | |

(52) U.S. Cl.
CPC ........... *G16H 50/20* (2018.01); *G06F 40/242* (2020.01); *G16H 10/60* (2018.01); *G16H 15/00* (2018.01); *G16H 70/20* (2018.01); *G06F 40/211* (2020.01); *G06F 40/30* (2020.01)

(58) Field of Classification Search
CPC combination set(s) only.
See application file for complete search history.

(56) References Cited

U.S. PATENT DOCUMENTS

| | | | |
|---|---|---|---|
| 2006/0271556 A1 | 11/2006 | Mukherjee et al. | |
| 2009/0024615 A1 | 1/2009 | Pedro et al. | |
| 2009/0099870 A1* | 4/2009 | Wilkinson | G06F 17/276 705/3 |
| 2009/0156947 A1* | 6/2009 | Seward | G06F 19/321 600/508 |
| 2010/0172567 A1 | 7/2010 | Prokoski | |
| 2014/0330586 A1* | 11/2014 | Riskin | G06F 17/2765 705/3 |
| 2015/0006199 A1* | 1/2015 | Snider | G06F 19/322 705/3 |

(Continued)

OTHER PUBLICATIONS

Coden et al., Automatically extracting cancer disease characteristics from pathology reports into a Disease Knowledge Representation Model, Oct. 2009, Journal of Biomedical Informatics, vol. 42, Issue 5, pp. 937-949.*

(Continued)

*Primary Examiner* — Devin C Hein
(74) *Attorney, Agent, or Firm* — McCarter & English LLP; Beverly W. Lubit

(57) ABSTRACT

A system, nontransitory computer readable medium, and method are provided for extracting data from unstructured medical text. Data points are identified in unstructured medical text, where the data points are determined using a dictionary database. A value associated with each of the data points is determined from the unstructured medical text. Each of the data points is mapped to its respective value for extraction from the unstructured medical text.

29 Claims, 6 Drawing Sheets

(56) References Cited

U.S. PATENT DOCUMENTS

2015/0100341 A1* 4/2015 Pecora .............. G06F 19/36
                                                  705/2
2017/0061086 A1   3/2017 Pecora

OTHER PUBLICATIONS

Weinstat-Saslow D., et al., "Angiogenesis and colonization in the tumor metastatic process: basic and applied advances", The FASEB Journal, 1994, vol. 8, pp. 401-407.
Boon T, et al., "Human tumor antigens recognized by T lympocytes", J. Exp. Med. 1996, vol. 183, pp. 725-729.
Clarke M.F., "Self-renewal and solid-tumor stem cells", Biology of Blood and Marrow Transplantation, 2005, vol. 11, pp. 14-16.
Hall A, "Oncogenes—implications for human cancer: a review", Journal of Royal Society of Medicine, 1984, vol. 77, pp. 410-416.
Khanna R., "Tumor surveillance: Missing peptides and MHC molecules", Immunology and Cell Biology, 1998, vol. 76, pp. 20-26.
Li C.Y., et al., "Role of incipient angiogenesis in cancer metastasis", Cancer and Metastasis Reviews, 2000, vol. 19, pp. 7-11.
Nestle F.O., "Dendritic cell vaccination for cancer therapy", Oncogene, 2000, vol. 19, pp. 6673-6679.
Stine Z.E., et al., "MYC, Metabolism, and Cancer", Cancer Discov., 2015, vol. 5, pp. 1024-1039.
Vile R., "Tumour suppressor genes", BMJ, 1989, vol. 298, pp. 1335-1336.
Welch, Danny R. "Tumor Heterogeneity—A 'Contemporary Concept' Founded on Historical Insights and Predictions," Cancer Research, vol. 76, issue 1 (Jan. 1, 2016) pp. 4-6.
International Search Report and Written Report from PCT/US2018/13118 dated Mar. 30, 2018.

* cited by examiner

300

DATE OF SERVICE: 05/12/2016 CHIEF COMPLAINT: The patient is a 57-year-old woman who presents in for evaluation and management of stage IA left upper outer quadrant breast cancer. HISTORY OF PRESENT ILLNESS: The history of present illness is well characterized in the initial/consult note. T1b N0, stage IA left breast cancer post left lumpectomy, Oncotype 12, triple negative, high Ki-67 with a positive P53. She presents today to continue Zoladex and Aromasin therapy. Since her last evaluation, she reports she has been feeling well. 11/12/2015: Since she was here, her liver was abnormal. She stopped Lipitor. LFTs were worked up by a GI doctor. 02/11/2016: Left upper outer quadrant tumor. She has arthralgias and myalgias. She has a 1 cm tumor. We will do a BCI. 05/12/2016: She comes in. She hates the Aromasin. The problem is her BCI was low/low. She has only really been on the pills for about a year. She hates the Zoladex also. She has arthralgias, myalgias, etc., but she does not want to go on tamoxifen, she does not want her ovaries out. She did not experience the same level of anxiety during menopause. Mammogram is noted. ALLERGIES: Refer to the Allergy section within the Visit Navigator in the EMR. CURRENT MEDICATIONS: Refer to the Medication section within Chart Review in the EMR. Refer to the History section within the Visit Navigator in the EMR for past medical, surgical, social, family history and occupational hazards. The past medical history, past surgical history, occupational history, family history, allergies are all reviewed and are unchanged from the initial/consult note of 04/22/2015. ECOG/KPS: 0/100.

| Attribute | Value |
|---|---|
| DATE_OF_VISIT | 5/12/2016 |
| ICD_9 | 174.4 |
| STAGE | IA |
| CANCER_SITE | breast |
| ESTROGEN_RECEPTOR | negative |
| HER2NEU | negative |
| PROGESTERONE_RECEPTOR | negative |
| STAGING_TYPE | Pathological |
| ONCOTYPE | 12 |
| REGIONAL_LYMPH_NODE | No |
| TUMOR | T1b |
| KI_67 | high |
| P53 | positive |
| TUMOR_SIZE_CM | 1 |
| MENOPAUSAL_STATUS | post-menopause |
| DATE_OF_INITIAL_VISIT | 4/22/2015 |

Fig. 4

SYSTEM AND METHOD FOR EXTRACTING ONCOLOGICAL INFORMATION OF PROGNOSTIC SIGNIFICANCE FROM NATURAL LANGUAGE

FIELD OF THE INVENTION

The present invention relates generally to identifying and extracting (together referred to as abstraction) data from unstructured text, and more particularly to extracting prognostically significant data from unstructured medical text to provide useful oncologic information of prognostic significance, to validate the data from an oncologic standpoint, and to transform the data into information that can be further analyzed to provide actionable insights.

BACKGROUND OF THE INVENTION

Many discoveries have led to progress in reducing the incidence, morbidity and mortality of cancer. Some examples include the discovery of oncogenes (See, e.g., Hall, A., (1984) "Oncogenes—implications for human cancer: a review," J. Royal Soc'y of Med. 77: 410-16), tumor suppressor genes (See, e.g., Vile, R., (1989) "Tumour suppressor genes," Br. Med. J. 298 (6684): 1335-36), the role of tumor angiogenesis in cancer (See, e.g., Weinstat-Saslow, D., Steeg, P S, (1994) "Angiogenesis and colonization in the tumor metastatic process: basic and applied advances," FASEB J. 8(6): 401-7; Li, C Y, et al, (2000) "Role of incipient angiogenesis in cancer metastasis," Cancer Metastasis Rev. 19 (1-2): 7-11); cancer stem cells (see e.g., Clarke, M. F., "Self-renewal and solid-tumor stem cells," Biology of Blood and Marrow Transplantation 11: 14-16 (2005); metabolic derangements in cancer cells (See, e.g., Stine, Z E et al, (2015) "MYC, metabolism and cancer," Cancer Discov. 5 (10): 1024-39); and discoveries in tumor immunology (See, e.g., Nestle, F O, (2000) "Dendritic cell vaccination for cancer therapy," Oncogene 19 (56): 6673-9; Khanna, R., (1998) "Tumour surveillance: Missing peptides and MHC molecules, "Immunol & Cell Biol. 76: 20-26; Boon, T., van der Bruggen, P., (1996) "Human tumor antigens recognized by T. Lymphocytes," J. Exp. Med. 183 (30): 725-29). Each discovery, which has helped to shed light on how normal cells become tumors and how tumors grow, invade, and metastasize, has led to more complexities. As a result of this expanding knowledge base, significant advances have been made in cancer care, so that even when cure is not possible, many cancers can be controlled and managed for long periods of time.

A very high percentage of oncologic data is in an unstructured text format. For example, a doctor evaluating an oncologic condition of a patient typically records notes of the evaluation in the patient's medical records in the form of a natural language, such as, e.g., English. The identification and extraction of prognostically significant data from the unstructured oncologic text is useful for further analysis that transforms the data into information that can be further analyzed to provide actionable insights.

Conventionally, the identification and extraction of all prognostically significant data from unstructured oncologic text is manually performed by humans reviewing the unstructured oncologic text. However, the manual identification and extraction of prognostically significant data from the unstructured oncologic text is difficult, time-consuming, and error-prone. The scale of the unstructured oncological text further adds to these problems. Further, while approaches for natural language extraction currently exist, these approaches are unable to extract prognostically significant data from unstructured oncologic text due to the complexity associated with oncology.

The difficulty in identifying and extracting prognostically significant data from the unstructured oncologic text results in a downstream issue of not being able to convert the unstructured oncological text into useful oncological information of prognostic significance.

SUMMARY

In accordance with one or more embodiments, an extraction system is provided for extracting prognostically significant data from unstructured text comprising medical data. The extraction system may be implemented for complex data, such as, e.g., oncologic data. Advantageously, the extraction system extracts prognostically significant data from unstructured text to allow for further processing, e.g., to validate the data from an oncologic standpoint, and to transform the data into information that can be further analyzed derive actionable insights.

In accordance with one or more embodiments, a system and method are provided for extracting data from unstructured medical text. Data points are identified in unstructured medical text, where the data points are determined from a dictionary database. A value associated with each of the data points is determined from the unstructured medical text. Each of the data points is mapped to its respective value for extraction from the unstructured medical text.

In accordance with one or more embodiments, the unstructured medical text may be sentences or phrases based on grammar rules of a natural language (e.g., English). For example, the unstructured medical text may be notations regarding a patient by a doctor. Alternatively, the unstructured medical text may include unstructured oncologic text.

In accordance with one or more embodiments, the dictionary database is generated (e.g., as a preprocessing step). A plurality of data points is received that is known to be diagnostically and prognostically significant (e.g., as identified by the doctor evaluating the patient, other doctors or medical experts, or advisory boards). Equivalent data points of the plurality of data points are determined. The equivalent data points are data points that are synonyms of the plurality of data points or morphological variations of the plurality of data points. The plurality of data points and the equivalent data points are stored to generate the dictionary database.

In accordance with one or more embodiments, each of the data points may be mapped to its respective value to generate attribute-value pairs. The mapping may store the attribute-value pairs as a list of attribute-value pairs, a collection of tuples, a table, or any other suitable data structure.

In accordance with one or more embodiments, the data points (i.e., attributes in the attribute-value pairs) are standardized by assigning the data points a corresponding unified medical language system (UMLS) code.

In accordance with one or more embodiments, the data points and their respective values are validated to ensure integrity. For example, the data points and their respective values may be validated by identifying inconsistencies with the set of data points and values or by identifying data points having a respective value that cannot be correct.

In accordance with one or more embodiments, the data points and their respective values are modelled to transform the data into information that can be further analyzed to provide actionable insights.

In accordance with one or more embodiments, a nodal address is assigned to a patient based on the data points and their respective values In accordance with one aspect, the described invention provides a method for extracting objective oncologic data of prognostic significance from subjective unstructured medical text in a natural language, comprising: A. receiving input comprising (i) one or more lists of data points; (ii) unstructured medical text comprising unstructured oncologic text and (iii) a database comprising an exhaustive dictionary of medical knowledge that identifies one or more data points as significant to diagnosis and prognosis; B. processing the inputs in A to generate lists of attribute-value pairs by: (a) identifying in the unstructured medical text data points and equivalents of the data points that are significant for diagnosis and prognosis; (b) extracting from the unstructured medical text all facts of known importance associated with words or phrases in the unstructured text that are syntactically or semantically dependent on or related to the extracted data points; (c), associating the extracted data points with the words or phrases in the unstructured text that are syntactically or semantically dependent on, or related to, the extracted data points; (d) mapping each extracted data point (attribute) with its syntactically or semantically dependent word or phrase (value) in (c) to generate attribute value pairs; (e) standardizing each attribute in the attribute-value pairs according to a code that represents each attribute; (C) validating the standardized attribute-data pairs to ensure oncologic integrity by: identifying inconsistencies between standardized attribute pairs; and identifying medical errors; (D) outputting a list of validated, standardized attribute-value pairs; and (E) modeling the validated standardized attribute-value pairs for best fit analysis of the oncologic data. In one embodiment, the method further comprises (E) based on the list of attribute-value pairs generated in B, classifying like personal health information, and grouping types of patients in the patient population based on the personal health information associated with the patient population as belonging to a plurality of nodal addresses by (1) representing each nodal address as a discrete punctuated string of digits comprising a prefix, a middle, and a suffix that represent a set of preselected variables that partition sorted personal health information for each patient in the patient population using a sorting filter to provide a sorted set of personal health information for that population, and to identify patients satisfying each parameter in the patient population, and classified like personal health information into a clinically relevant set of health information; (2) reducing trillions of possible permutations to a reduced number of clinically meaningful permutations based on the discrete punctuated string of digits representing each nodal address that enable analysis of first behavioral and then consequent clinical and cost outcome variance from an ideal value, expressed as best clinical outcome at lowest possible cost, in a requisite time needed to alert for necessary care and avoidance of unnecessary care, thereby increasing the value of care, meaning better clinical outcomes at a lowest possible cost; (3) allowing the user (a') to identify certain of the personal health information as a desired set of characteristics, and (b') to add one or more attribute(s) to the personal health information to identify the personal health information of each patient as being on an equal level of importance to other health information in the patient population database, (4) reducing processing requirements and time for processing to make real-time monitoring of medical provider performance efficient based on the discrete punctuated string of digits representing each nodal address and based on the reduction in permutations; and (F) generating a unique nodal address for each combination of diagnostically and prognostically significant data points.

In accordance with some embodiments, (a) the unstructured medical text is stored as an image or as text; or (b) the unstructured medical text is a notation from a doctor in form of sentences or phrases based on grammar rules relating to an oncologic condition of a patient evaluated by the doctor; or (c) the unstructured oncologic text includes one or more of demographic parameters, a simple indicator, a numerically based parameter, a standards based parameter, dates of service, medical history, medicines, diagnoses, allergies, immunization status, lab tests results, vital signs, and personal statistics.

In accordance with some embodiments, the equivalents of the data points comprise synonyms and morphological variations of the data points.

In accordance with some embodiments, the code that represents each attribute comprises a unified medical language system (UMLS) code.

In accordance with some embodiments, the outputting is on a per patient basis, a per event basis or both.

In some embodiments, the outputting on a per event basis comprises e.g., diagnosis, treatment, progression (e.g., ECOG), or clinical outcome.

In accordance with some embodiments, clinical outcome comprises one or more of overall survival (OS), progression free survival (PFS), response metrics, quality of life metrics, incidence of drug toxicity, severity of drug toxicity, delivered dose intensity, drugs received, drug interval, drug duration, cost of care, or death In accordance with some embodiments, the outputting is in form of a java script output notation (JSON) document.

In accordance with another aspect, the described invention provides a non-transitory computer readable storage medium storing computer program instructions for extracting objective oncologic data of prognostic significance from unstructured medical text in a natural language, which, when executed on a processor, cause the processor to perform operations comprising: A. receiving input comprising (i) one or more lists of data points; (ii) unstructured medical text comprising unstructured oncologic text and (iii) a database comprising an exhaustive dictionary of medical knowledge that identifies one or more data points as significant to diagnosis and prognosis; B. processing the inputs in A to generate lists of attribute-value pairs by: (a) identifying in the unstructured medical text data points and equivalents of the data points that are significant for diagnosis and prognosis; (b) extracting from the unstructured medical text all facts of known importance associated with words or phrases in the unstructured text that are syntactically or semantically dependent on or related to the extracted data points; (c) associating the extracted data points with the words or phrases in the unstructured text that are syntactically or semantically dependent on, or related to, the extracted data points; (d) mapping each extracted data point (attribute) with its syntactically or semantically dependent word or phrase (value) in (c) to generate attribute value pairs; (e) standardizing each attribute in the attribute-value pairs according to a code that represents each attribute; (C) validating the standardized attribute-data pairs to ensure oncologic integrity by: identifying inconsistencies between standardized attribute pairs; identifying medical errors; (D) outputting a list of validated, standardized attribute-value pairs; and (E) modeling the validated standardized attribute-value pairs for best fit analysis of the oncologic data.

In accordance with some embodiments, the non-transitory computer readable storage medium which, when executed on a processor, causes the processor to perform operations further comprising (E) based on the list of attribute-value pairs generated in B, classifying like personal health information, and grouping types of patients in the patient population based on the personal health information associated with the patient population as belonging to a plurality of nodal addresses by: (i) representing each nodal address as a discrete punctuated string of digits comprising a prefix, a middle, and a suffix that represent a set of preselected variables that partition sorted personal health information for each patient in the patient population using a sorting filter to provide a sorted set of personal health information for that population, and to identify patients satisfying each parameter in the patient population, and classified like personal health information into a clinically relevant set of health information; (ii) reducing trillions of possible permutations to a reduced number of clinically meaningful permutations based on the discrete punctuated string of digits representing each nodal address that enable analysis of first behavioral and then consequent clinical and cost outcome variance from an ideal value, expressed as best clinical outcome at lowest possible cost, in a requisite time needed to alert for necessary care and avoidance of unnecessary care, thereby increasing the value of care, meaning better clinical outcomes at a lowest possible cost; (iii) allowing the user (a') to identify certain of the personal health information as a desired set of characteristics, and (b') to add one or more attribute(s) to the personal health information to identify the personal health information of each patient as being on an equal level of importance to other health information in the patient population database, (iv) reducing processing requirements and time for processing to make real-time monitoring of medical provider performance efficient based on the discrete punctuated string of digits representing each nodal address and based on the reduction in permutations; and (F) generating a unique nodal address for each combination of diagnostically and prognostically significant data points.

In accordance with some embodiments, (a) the unstructured medical text is stored as an image or as text; or (b) the unstructured medical text is a notation from a doctor in form of sentences or phrases based on grammar rules relating to an oncologic condition of a patient evaluated by the doctor; or (c) the unstructured oncologic text includes one or more of demographic parameters, a simple indicator, a numerically based parameter, a standards based parameter, dates of service, medical history, medicines, diagnoses, allergies, immunization status, lab tests results, vital signs, personal statistics.

In accordance with some embodiments, the equivalents of the data points comprise synonyms and morphological variations of the data points.

In accordance with some embodiments, the code that represents each attribute comprises a unified medical language system (UMLS) code.

In accordance with some embodiments, the outputting is on a per patient basis, a per event basis or both.

In accordance with some embodiments, the outputting on a per event basis comprises e.g., diagnosis, treatment, progression (e.g., ECOG), or clinical outcome.

In accordance with some embodiments, clinical outcome comprises one or more of overall survival (OS), progression free survival (PFS), response metrics, quality of life metrics, incidence of drug toxicity, severity of drug toxicity, delivered dose intensity, drugs received, drug interval, drug duration, cost of care, or death In accordance with some embodiments, the outputting is in form of a java script output notation (JSON) document.

In accordance with accordance with another aspect, the described invention provides a system for extracting objective oncologic data of prognostic significance from unstructured medical text in a natural language, comprising: a first database comprising an exhaustive dictionary of medical knowledge that identifies one or more data points as significant to diagnosis and prognosis; a second database comprising personal health information data for a population of human subjects; wherein the first and second database are communicatively linked using a common patient identifier and through the use of database access using the common patient identifier; an extraction system comprising: a computer server comprising a processor comprising a clinical outcome tracking and analysis module communicatively linked to the first database, the second database and the network; and a memory to store computer program instructions, the computer program instructions when executed on the processor cause the processor to perform operations comprising: A. receiving input comprising (i) one or more lists of data points; (ii) unstructured medical text comprising unstructured oncologic text and (iii) a database comprising an exhaustive dictionary of medical knowledge that identifies one or more data points as significant to diagnosis and prognosis B. processing the inputs in A to generate lists of attribute-value pairs by: (a) identifying in the unstructured medical text data points and equivalents of the data points that are significant for diagnosis and prognosis; (b) extracting from the unstructured medical text all facts of known importance associated with words or phrases in the unstructured text that are syntactically or semantically dependent on or related to the extracted data points; (c) associating each extracted data point with the words or phrases in unstructured text that are syntactically or semantically dependent on, or related to, each extracted data point to produce a set of extracted data points that are of prognostic significance; (d) mapping each extracted data point (attribute) with its syntactically or semantically dependent word or phrase (value) in (c) to generate attribute value pairs; (e) standardizing each attribute in the attribute-value pairs according to a code that represents each attribute; (C) validating the standardized attribute-data pairs to ensure oncologic integrity by: identifying inconsistencies between standardized attribute pairs; and identifying medical errors; (D) outputting a list of validated, standardized attribute-value pairs; and (E) modeling the validated standardized attribute-value pairs for best fit analysis of the oncologic data.

In accordance with some embodiments, the computer program instructions of the system when executed on the processor cause the processor to perform operations further comprising (E) based on the list of attribute-value pairs generated in B, classifying like personal health information, and grouping types of patients in the patient population based on the personal health information associated with the patient population as belonging to a plurality of nodal addresses by: (i) representing each nodal address as a discrete punctuated string of digits comprising a prefix, a middle, and a suffix that represent a set of preselected variables that partition sorted personal health information for each patient in the patient population using a sorting filter to provide a sorted set of personal health information for that population, and to identify patients satisfying each parameter in the patient population, and classified like personal health information into a clinically relevant set of health information; (ii) reducing trillions of possible permutations to a reduced number of clinically meaningful permutations based on the discrete punctuated string of digits representing each nodal address that enable analysis of first behavioral and then consequent clinical and cost outcome variance from an ideal value, expressed as best clinical outcome at lowest possible cost, in a requisite time needed to alert for necessary care and avoidance of unnecessary care, thereby increasing the value of care, meaning better clinical outcomes at a lowest possible cost; (iii) allowing the user (a') to identify certain of the personal health information as a desired set of characteristics, and (b') to add one or more attribute(s) to the personal health information to identify the personal health information of each patient as being on an equal level of importance to other health information in the patient population database, (iv) reducing processing requirements and time for processing to make real-time monitoring of medical provider performance efficient based on the discrete punctuated string of digits representing each nodal address and based on the reduction in permutations; and (F) generating a unique nodal address for each combination of diagnostically and prognostically significant data points.

In accordance with some embodiments of the system, (a) the unstructured medical text is stored as an image or as text; or (b) the unstructured medical text is a notation from a doctor in form of sentences or phrases based on grammar rules relating to an oncologic condition of a patient evaluated by the doctor; or (c) the unstructured oncologic text includes one or more of demographic parameters, a simple indicator, a numerically based parameter, a standards based parameter, dates of service, medical history, medicines, diagnoses, allergies, immunization status, lab tests results, vital signs, personal statistics; or (d) the equivalents of the data points comprise synonyms and morphological variations of the data points; or (e) the code that represents each attribute comprises a unified medical language system (UMLS) code; or (f) the outputting is on a per patient basis, a per event basis or both.

In accordance with some embodiments of the system the outputting on a per event basis comprises e.g., diagnosis, treatment, progression (e.g., ECOG), or clinical outcome.

In accordance with some embodiments of the system, clinical outcome comprises one or more of overall survival (OS), progression free survival (PFS), response metrics, quality of life metrics, incidence of drug toxicity, severity of drug toxicity, delivered dose intensity, drugs received, drug interval, drug duration, cost of care, or death In accordance with some embodiments of the system, the outputting is in form of a java script output notation (JSON) document.

These and other advantages of the present disclosure will be apparent to those of ordinary skill in the art by reference to the following Detailed Description and the accompanying drawings.

BRIEF DESCRIPTION OF THE DRAWINGS

FIG. 3 shows an example of unstructured oncologic text, in accordance with one embodiment;

FIG. 4 shows an exemplary table of attribute-value pairs, in accordance with one embodiment;

DETAILED DESCRIPTION

Figure 1:
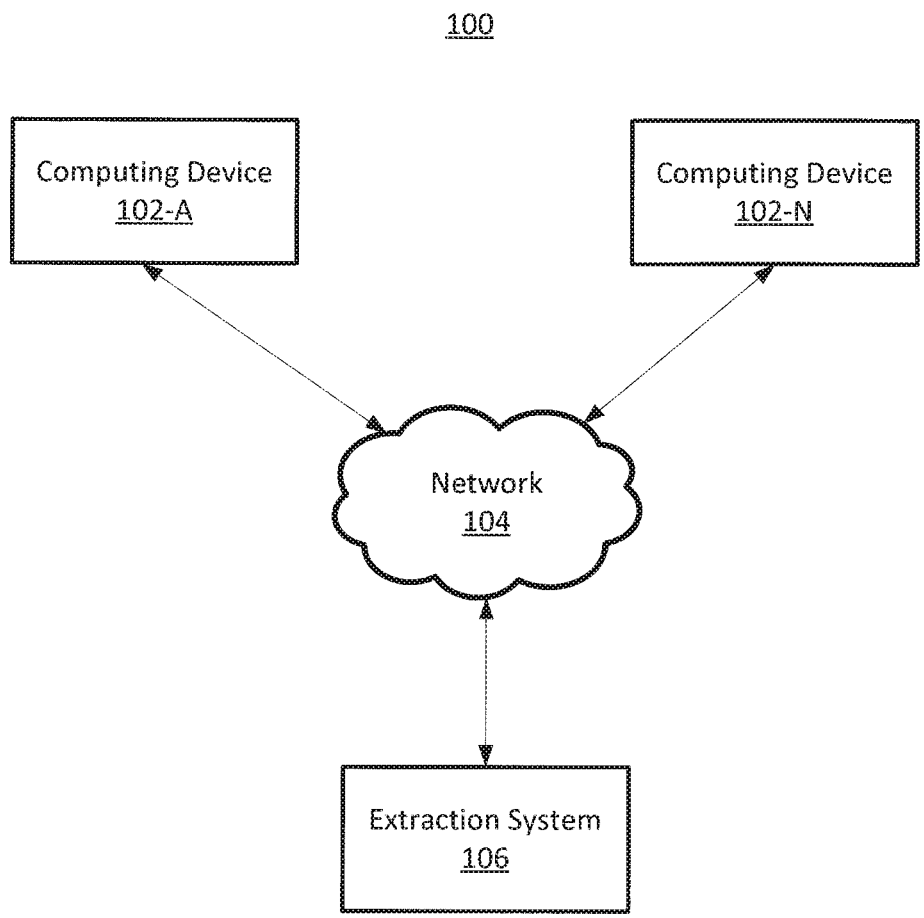
FIG. 1 shows a high-level diagram of a communications system, in accordance with one embodiment.

The term "condition", as used herein, refers to a variety of health states and is meant to include disorders or diseases caused by any underlying mechanism or disorder.

The term "data integrity" as used herein refers to the extent to which all data are complete, consistent, and accurate throughout the data.

The term "diagnosis" and its other grammatical forms is used herein to refer to a determination of the nature of a disease.

Grammar Rules:

In any natural language there are rules, termed "grammar rules", needed for a reader or listener to make sense of communication using that language. Basic grammar rules are the rules referring to sentence structure, the basic parts of speech, and punctuation. The following are exemplary basic rules of English grammar.

Sentence Structure

1. A group of words that can stand alone and make a complete thought that consists of a subject and a predicate is an independent clause or a sentence. The subject is the thing that is the focus of the sentence. The predicate tells the action that the subject is taking or something about the subject.

2. A compound sentence is one with two independent clauses joined by a conjunction or a semicolon.

3. The verb and the noun, or the verb and the object, of a sentence should agree, e.g., a singular subject needs a singular predicate.

4. A group of words that does not have a subject and predicate is a dependent clause.

5. Paragraphs are used to divide long segments of writing about the same subject or line of thought.

Parts of Speech

1. A noun is a part of speech that denotes a person, animal, place, thing, quality, idea, activity, or feeling. A noun can be singular, plural, or show possession.

2. A pronoun is a word that takes the place of a noun, like: "I", "he", "she", "it", "you", or "they."

3. A verb is a part of speech used to describe an action, state of being or occurrence, and can be a main verb or a helping verb. Verbs also indicate tense and sometimes change their form to show past, present, or future tense. State of being (linking) verbs link the subject to the rest of the sentence.

4. An adjective is a part of speech that describes, identifies or further defines a noun or a pronoun. For example, an adjective can add meaning by telling how much, which one, what kind, or describing it in other ways. An article (e.g., "a", "an", or "the") is an adjective used to point out or refer to a noun. "A" and "an" are indefinite articles. "The" is a definite article.

5. An adverb is a part of speech that modifies or qualifies a verb, an adjective, or other adverb or a word group telling, e.g., when, where, how, why, in what manner, or to what extent an action is performed.

6. A preposition is a part of speech that shows a relationship between a noun or pronoun and some other nearby word or element in the rest of the sentence. A sentence should not end with a preposition.

7. A conjunction is a part of speech used to connect clauses, phrases, or sentences, or to coordinate words in the same clause. A conjunction should not be used to start a sentence.

Punctuation Rules

1. All sentences must start with a capital, or upper case, letter.

2. Titles of people, books, magazines, movies, specific places, etc. are capitalized. Organizations and compass points are capitalized.

3. Every sentence needs a punctuation mark (e.g., a period, exclamation mark, or question mark) at the end of it.

4. An apostrophe is a punctuation mark used to indicate either possession or the omission of letters or numbers.

5. A colon is used to separate a sentence from a list of items, between two sentences when the second one explains the first, and to introduce a long direct quote.

6. A comma separates things in a series and goes wherever there is a pause in the sentence. For example, commas surround the name of a person being addressed, separate the day of the month from the year in a date, and separate a town from the state. When the clauses of a compound sentence are joined by a conjunction, a comma is usually placed before the conjunction.

7. Parentheses are a pair of round brackets used to mark off a parenthetical word or phrase. A parenthetical word or phrase is a word, clause or sentence inserted as an explanation or an aside into a passage that is grammatically complete without it.

8. A semicolon is used to take the place of a conjunction, and is placed before introductory words like "therefore" or "however." It is also used to separate a list of things if there are commas within each unit.

"ICD-10" The International Statistical Classification of Diseases and Related Health Problems 10th Revision (ICD-10) is a coding of diseases, signs and symptoms, abnormal findings, complaints, social circumstances and external causes of injury or diseases, as classified by the World Health Organization (WHO). The code set allows more than 14,400 different codes and permits the tracking of many new diagnoses. ICD-10 is an updated version of the ICD-9 code sets. Health plan systems and health care providers are required by the Health Insurance Portability and Accountability Act (HIPAA) to use a standard code set to indicate diagnoses and procedures on transactions. For diagnoses, the ICD-9-CM code set is used. The ICD-9-CM procedure code set is used for inpatient hospital procedures. For other types of procedures, health plans and providers use Current Procedural Terminology (CPT) or Healthcare Common Procedure Coding System (HCPCS) codes, which explain the soon-to-be required ICD-10-CM codes for diagnoses and ICD-10-PCS codes for inpatient hospital procedures.

The term "information extraction" as used herein refers to the act of extracting, by computer, recognizable information from documents written in a human language. It is distinguished from "information retrieval" which refers to the act of identifying, by computer, documents written in a human language that are relevant to some specific question. This often includes, e.g., statistical analysis of vocabulary (to determine subject matter) and a considerable amount of natural language processing. It is easier to process natural-language texts in a way that falls short of full understanding, but still allows some of the meaning to be extracted.

The term "natural language" as used herein refers to an actual language as used in ordinary discourse to communicate in everyday life.

The term "natural language processing" as used herein refers to the use of computers to process information expressed in human (natural) languages. Getting computers to understand a human language, which includes signal processing/speech recognition, syntactic analysis, or parsing to determine sentence structure, semantic analysis to determine meaning, and pragmatics/knowledge representation to encode the meaning into a computer, language is a difficult, largely unsolved problem.

The term "oncologic" as used herein refers to relating to the branch of medicine that deals with the physical, chemical and biologic properties and features of neoplasms, including causation, pathogenesis and treatment.

The term "parsing" as used herein refers to the analysis, by computer, of the structure of statements in a human or artificial language. Programs that accept natural language input generally have to parse sentences in human languages.

The term "pragmatics" as used herein refers to a branch of linguistics concerned with insights for determining a meaning, whether inferred or implied, in a communication from a number of factors, including context, knowledge of the situation in which the communication occurs, and intent, to overcome ambiguity in the communication.

The term "processing" as used herein refers to both interpretation (meaning understanding) and generation (meaning production).

The term "prognosis" and its other grammatical forms as used herein refers to a prediction about the probable course and/or outcome of a disease. The term "prognostic" as used herein refers to relating to prognosis; a symptom upon which a prognosis is based or one indicative of the likely outcome The term "speech recognition" as used herein refers to use of computers to recognize spoken words. The same spoken word does not produce entirely the same sound waves when pronounced by different individuals, or even when pronounced by the same person on more than one occasion. The computer must digitize the sound, transform it to discard unneeded information, and try to match it with words stored in a dictionary. Most speech recognition systems are speaker-dependent; they have to be trained to recognize a particular person's speech and then can distinguish thousands of words but only the words on which they were trained). Speaker independent speech recognition is less effective.

The term "semantic analysis" as used herein refers to the use of contextual clues surrounding words and phrases in natural language text so that the computer can better understand the implied or practical meaning and relevance of that text. Machine-driven semantic analysis can extract relevant and useful information from large bodies of unstructured data; find an answer to a question without having to ask a human; discover the meaning of colloquial speech, and uncover specific meanings of words that are not commonly used in our own language.

The term "syntax" as used herein refers to the set of rules that specify how the symbols of a language can be put together to form meaningful statements. A "syntax error" is a place in a program where the syntax rules of the programming language were not followed.

FIG. 1 shows a high-level diagram of a communications system 100, in accordance with one or more embodiments. Communications system 100 includes one or more computing devices 102-A, . . . , 102-N (collectively referred to as computing devices 102). Computing devices 102 may comprise any type of computing device, such as, e.g., a computer, a workstation, a tablet, a mobile device, a server, or a database. Computing devices 102 are operated by users for communicating via network 104. Network 104 may include any type of network or combination of different types of networks, and may be implemented in a wired and/or a wireless configuration. For example, network 104 may include one or more of the Internet, an intranet, a local area network (LAN), a wide area network (WAN), a Fibre Channel storage area network (SAN), a cellular communications network, etc.

In one embodiment, a user may interact with computing device 102 for the processing of data. For example, a user, such as a doctor or other medical professional, may interact with computing device 102 to store medical information of a patient in a patient medical record database (not shown). The medical information is typically input into computing device 102 as unstructured data (e.g., text or images). For example, the unstructured text may be in the form of sentences or phrases generally following English grammar rules.

Conventionally, unstructured medical text is difficult to process programmatically, because virtually none of the information in unstructured medical text is stored in information fields. As such, the identification and extraction of prognostically significant data from the unstructured medical text must be performed manually. The manual identification and extraction of prognostically significant data from unstructured medical text is difficult, time-consuming, and error prone. This is particularly true for unstructured oncologic text due to the complexity of oncology.

Advantageously, embodiments of the present invention provide for an extraction system 106, which is configured to generate a dictionary of prognostically significant data points (e.g., data points of medical significance from a prognostic standpoint) and to identify and extract prognostically significant data points from unstructured medical text using the dictionary, thereby transforming subjective data into objective data. Extraction system 106 in accordance with embodiments of the invention thus provides for improvements in computer related technology by facilitating the identification and extraction of prognostically significant data points from unstructured medical text.

It should be understood that while embodiments of the present invention described herein may be discussed in terms of oncologic data, the embodiments of the present invention are not so limited. Embodiments of the present invention may be implemented for the identification and extract of relevant data from any type of unstructured medical data.

Figure 2:
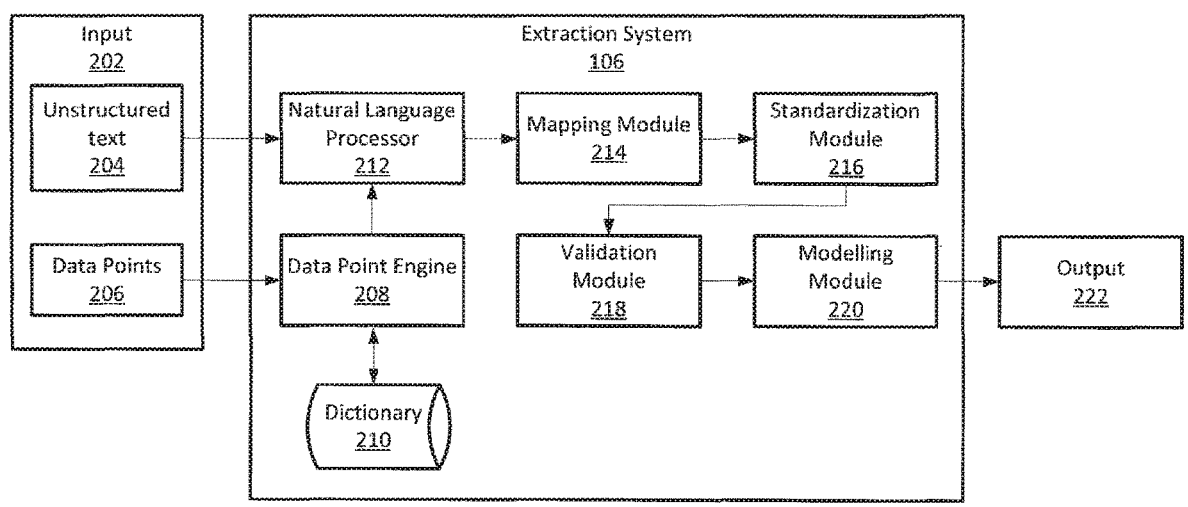
FIG. 2 shows a system architecture of an extraction system for identifying and extracting prognostically significant data from unstructured text, in accordance with one embodiment.

FIG. 2 illustratively depicts a system architecture 200 of extraction system 106 for the identification and extraction of prognostically significant data from unstructured text, in accordance with one or more embodiments.

Extraction system 106 receives input 202, e.g., from a user (e.g., a doctor or medical professional) interacting with computing device 102 via network 104 in FIG. 1. Input 202 includes unstructured data, such as unstructured text 204, a list of data points from advisory boards, and an exhaustive dictionary of medical knowledge from advisory boards of what is significant to diagnosis, prognosis or both in the context of e.g., oncology. Unstructured text 204 is any textual data that is not structured (such as, e.g., in fields or tables). For example, unstructured text 204 may be in the form of sentences or phrases generally following grammar rules (e.g., English grammar rules). In some embodiments, the unstructured data of input 202 includes unstructured image data (e.g., charts). In one embodiment, the unstructured image data is converted to unstructured text 204, e.g., using methods known in the art.

In one embodiment, unstructured text 204 includes unstructured medical text of a patient. For example, the unstructured medical text may be notations of a patient from a doctor or other medical professional recorded in the patient's medical records. The unstructured medical text of the patient may include, for example, demographic parameters. Exemplary parameters include, without limitation, sex, age, ethnicity, comorbidities, tobacco use, medical record number, source of insurance, primary care medical professional, referring medical professional, hospital, approved service vendors (e.g., pharmacy), disease specific clinical and molecular phenotype, therapy intent, stage of therapy with respect to progression of disease, biomarkers and cost of care. For example, the element Eastern Cooperative Oncology Group (ECOG) performance status/quality of life metrics refers to a scale by which the quality of life of the patient over time can be tracked. It is part of the demographic parameter disease specific clinical molecular phenotype, i.e., the stage of a patient's health at the start of therapy. For example, a comparison of ECOG at start of therapy (e.g., ECOG of 3), with ECOG after therapy (e.g., ECOG of 2) reflects the effect of the therapy.

According to some embodiments, the unstructured medical text may be a simple indicator (e.g., positive, negative, not accessed), a numerically based parameter (e.g., tumor size), a standards based parameter (e.g., tumor grade), dates of service, medical history, medication, diagnoses, allergies, immunization status, laboratory test results, vital signs, personal statistics, or any other suitable medical information of the patient.

In one embodiment, the unstructured medical text of the patient is unstructured oncologic text. Unstructured oncologic text is particularly difficult to programmatically process due to the complexity of oncology.

FIG. 3 illustratively shows an example of unstructured oncologic text 300, in accordance with one embodiment. Unstructured oncologic text 300 may be unstructured text 204. Unstructured oncologic text 300 may contain notations from a doctor recorded in a patient's medical records after evaluating the patient for breast cancer. Unstructured oncologic text 300 includes, e.g., a chief complaint of the patient, a history of the present illness, dates of service, allergies of the patient, and current medications of the patient.

Input 202 of FIG. 2 also includes data points 206. Data points 206 are data points that are significant for diagnosis and prognosis. For example, where extraction system 106 is configured to analyze unstructured text 204 to determine oncologic information of diagnostic and prognostic significance, data points 206 are data points of oncologic significance. Data points 206 may be determined by the particular doctor evaluating the patient, other doctors or medical experts, advisory boards, medical journals or publications, etc. An example of data points 206 that are significant for breast cancer diagnosis and prognosis include presence (+) or absence (−) of the estrogen receptor (ER), human epidermal growth factor receptor 2 (Her2 receptor), and progesterone receptor (PR).

Data point engine 208 of extraction system 106 is configured to receive data points 206 and identify equivalent data points of data points 206. Equivalent data points of data points 206 are data points that are synonyms of data points 206 or morphological variations of data points 206. The equivalent data points of data points 206 may be identified by, e.g., referencing a list, a table, or a database of equivalent data points. In one example, data point engine 208 identifies the following equivalent data points for the data point of estrogen receptor: human estrogen receptor and ER. In one embodiment, the equivalent data points of data point 206 are data points that, in combination, are equivalent to data point 206. For example, a diagnosis of triple negative breast cancer means that estrogen receptors, Her2 receptors, and progesterone receptors are not present. Data point engine 208 thus identifies the following equivalent data points for the data point of triple negative breast cancer: ER neg, HER2 neg, and PR neg.

Data point engine 208 stores data points 206 and the identified equivalent data points of data points 206 in dictionary 210 (e.g., a dictionary database). Dictionary 210 thus provides for an exhaustive list of all data points that are significant for diagnosis or prognosis.

In one embodiment, data point engine 208 receives data points 206 and identifies equivalent data points of data points 206 to generate dictionary 210 in a preprocessing step. In this manner, extraction system 106 can analyze a plurality of inputs 202 of unstructured text 204 without having to regenerate dictionary 210 for each input 202. In one embodiment, instead of receiving data points 206 and identifying equivalent data points of data points 206 to generate dictionary 210, dictionary 210 is directly received as input 202 or was previously generated and stored in a database (not shown) and retrieved by extraction system 106 as necessary.

Natural language processor 212 receives unstructured text 204 and analyzes unstructured text 204 using dictionary 210 to extract all facts of known importance, e.g., cancer type, date of visit, ICD9 classification, stage, ER (+/−), Her2(+/−), PD (+/−). For example, natural language processor 212 may analyze unstructured text 204 to identify and extract prognostically significant data points in dictionary 210 that are present in unstructured text 204.

The extracted data points are associated with words or phrases in unstructured text 204 that are syntactically or semantically dependent on (or related to) the respective extracted data point. In one embodiment, natural language processor 212 determines the words or phrases from unstructured text 204 that are syntactically or semantically dependent on the extracted data points by applying probabilistic or semantic analysis.

The output of natural language processor 212 is a set of extracted data points, identified as being prognostically significant in dictionary 210, each associated words or phrases that are syntactically or semantically dependent. In one example, unstructured text 204 may state: "ER was positive." Natural language processor 212 would identify ER as being a significant data point (as indicated by dictionary 210) and determine that ER is syntactically dependent on the word "positive."

Mapping module 214 maps each extracted data point with its respective syntactically or semantically dependent word or phrase, as determined by natural language processor 212, to generate attribute-value pairs. In particular, each extracted data point is an attribute and their respective syntactically or semantically dependent word or phrase is the value. Thus, for the example where unstructured text 204 comprises "ER was positive," ER is the attribute and positive is the value. In another example, unstructured text comprises: "Tumor in lung. It was found to be 2 cm." Here, the attribute (i.e., tumor) and the value (i.e., 2 cm) are in two sentences. Mapping module 212 would recognize that "it" refers back to "tumor." The attribute-value pairs may be stored in any suitable data structure, such as, e.g., a collection of tuples (in the form of, e.g., attribute:value or <attribute, value>) or a table having rows of attributes and corresponding values.

FIG. 4 illustratively shows an exemplary table 400 of attribute-value pairs, in accordance with one embodiment. The attribute-value pairs in table 400 may be identified from unstructured medical text 300 in FIG. 3. Table 400 includes attributes 402 with corresponding values 402. Attributes 402 are prognostically significant data points extracted from unstructured medical text 300 using dictionary 210. Values 404 are syntactically or semantically dependent on the attribute 402 in unstructured medical text 300. Mapping module 214 maps the attributes with respective values and stores the mapping as table 400.

Standardization module 216 in FIG. 2 is configured to standardize the attributes in the attribute-value pairs. In one embodiment, the attributes are standardized according to the unified medical language system (UMLS), which is an industry accepted standard. The UMLS code for each attribute is obtained by looking up a database that has mapped the UMLS codes and the corresponding attributes (see, e.g., https://metamap.nlm.nih.gov/SemanticTypesAnd-Groups.shtml/ for a parsable list of semantic types and their abbreviations from the UMLS and a parsable list of semantic groups and their mappings to the semantic types, each of which is incorporated herein by reference). Each attribute is assigned the UMLS code that represents that particular attribute. For example, where UMLS code C12345 represents ER, the attribute in the attribute-value pair <ER, positive> is assigned UMLS code C12345. The attribute-value pair is thus standardized to <C12345, positive>. It should be understood that standardization module 216 may standardize the attributes according to any standard, and is not limited to UMLS.

Validation module 218 is configured to validate the standardized attribute-value pairs to ensure integrity. Validation is performed through the use of standard lists that map ICD9 codes to cancer types, and comparing attribute-value pairs with the cancer type referenced in the extracted data. In particular, validation module 218 may identify inconsistencies between standardized attribute-value pairs. Validation module 218 may also identify standardized attribute-value pairs that cannot be correct. Validation module 218 validates the standardized attribute-value pairs at the field level and amongst those fields. For example, a patient's performance is evaluated according to the Eastern Cooperative Oncology Group (ECOG) scale, ranging from Grade 0 (i.e., fully active) to Grade 5 (i.e., dead). A standardized attribute-value pair indicating ECOG is 7 cannot be correct. Validation module 218 will identify the attribute-value pair indicating ECOG is 7 for, e.g., manual review or correction or removal. In another example, if a patient is being evaluated for lung cancer, an attribute indicating an ICD9 code of 174.9 (referring to breast cancer) is inconsistent with the cancer type of the patient. Validation module 218 will identify the attribute-value pair indicating an ICD9 code of 174.9.

Modelling module 220 models the validated, standardized attribute-value pairs as a model that is optimal for analyzing and deriving actionable insights (i.e., a model that best fits analysis of the oncologic data). For example, a patient diagnosed with stage 1 cancer is subsequently diagnosed with stage 2 cancer. Modelling module 220 models the validated, standardized attribute-value pairs to identify the progression of the cancer from stage 1 to stage 2, thus providing actionable insights as the patient would have received different treatment for each stage. Modeling of the data is done in a fashion that enables grouping of data points that belong to a particular longitudinal point in the patient's journey through cancer. All data points that are required to enable diagnosis and prognosis analysis are grouped together. The result of the modeling is used to look up which data points are to be extracted from the free text.

Extraction system 106 analyzes input 202 to provide output 222. Output 222 includes a list of the validated, standardized attribute-value pairs. For example, output 222 may include a list attribute-value pairs in the format of attribute:value, <attribute, value>, or any other suitable format. In one embodiment, extraction system 106 receives input 202 to provide the list of attribute-value pairs as output 222 on a per patient basis. In one embodiment, for each patient, extraction system 106 also may provide the list of attribute-value pairs as output 222 on a per event basis (e.g., diagnosis, treatment, progression (e.g., ECOG), outcomes (e.g., overall survival (OS), progression free survival (PFS), toxicity). In one embodiment, clinical outcome comprise at least one of survival, response metrics, quality of life metrics, incidence of drug toxicity, severity of drug toxicity, delivered dose intensity, drugs received, drug interval, drug duration, cost of care, and death. Output 222 may be in the format of a java script output notation (JSON) document, however any other suitable format may also be employed.

From the exhaustive list of all data points, advantageously, extraction system 106 extracts significant data points from unstructured medical text 206. The extracted significant data points provide useful medical (e.g., oncologic) information of prognostic significance that can be used to provide actionable insights. Each clinical outcome tracking and analysis nodal address (CNA) is a subset of that list.

Like personal health information can be classified and types of patients in the patient population grouped based on personal health information associated with the patient population by generating and assigning a plurality of nodal addresses within a computer containing a processor comprising a first clinical outcome tracking and analysis module.

For example, a patient is classified into one or more Clinical outcome tracking and analysis Nodal Addresses (CNAs) based on the list of attribute-value pairs of output 222 determined by extraction system 106 from unstructured text 204 for that patient. The CNAs represent a set of preselected variables that can be used to classify groups of patients (or data) into clinically relevant sets. The list of attribute-value pairs of output 222 are used to generate a unique CNA for each combination of prognostically significant data points. When a patient is entered into the system, the patient is assigned the CNA which matches the attributes the patient has.

In one embodiment, the CNA is a list of variables (as a function of a letter representing the variable and a number representing the selection within the variable). For example, the letter A may represent the sex or gender variable and numbers 1 and 2 represent female and male patient, the letter B may represent the race variable and number 1 through 4 represent different races. Thus, a CNA may be represented as A1-2, B1-4, . . . , N1.

In another embodiment, the CNA is represented as a plurality of discrete strings of digits separated by periods, where each string of digits indicates one or more variables (e.g., disease, phenotype, therapy type, progression/track, sex, etc.). For example, a first string of digits may represent a particular disease, a second string of digits may represent a type of disease, a third string of digits may indicate a subtype of the disease, and a further string of digits may indicate a phenotype. Thus, in this example, the first string of digits may be 01 indicating cancer, the second string of digits may be 02 indicating breast oncology, a third string of digits may be 01 indicating breast cancer, and a fourth string of digits may be 1201 representing particular characteristics of a phenotype such that the nodal address is 01.02.01.1201. It should be understood that the nodal address may include any number of strings of digits and is not limited to four strings.

Each CNA may be associated with one or more bundles of predetermined patient care services (e.g., treatment plans). Each bundle may also be associated with one or more nodes. The services included in each bundle may be determined by one or more medical professionals, a hospital, a group, an insurance company, etc. to optimize patient care and/or cost. In one example, a bundle may indicate a number of imaging scans, a drug or choice of drugs, a schedule of when to administer the drugs, an operation or procedure, a number and frequency of follow up visits, etc. The bundling of patient care services may be particularly useful for risk contracting. For example, each bundle corresponding to a nodal address (associated with a particular disease) may have a predetermined cost allowing a user (e.g., doctor, patient, etc.) to choose an appropriate bundle. The cost may be determined or negotiated based on historical data associated with that particular disease or nodal address. Advantageously, the bundling of services provides cost certainty to an insurance company and/or hospital for a particular disease. This also reduces the cost of processing and maintaining records. Additionally, medical professionals will know ahead of time the predetermined course of treatment, which provides incentives to physicians to obtain better outcomes at lower costs.

Each nodal address reduces trillions of possible permutations to a reduced number of clinically meaningful permutations based on the discrete punctuated string of digits representing each nodal address. According to some embodiments, this enables analysis of first behavioral and then consequent clinical and cost outcome variance from an ideal value, expressed as best clinical outcome at lowest possible cost, in a requisite time needed to alert for necessary care and avoidance of unnecessary care, thereby increasing the value of care, meaning better clinical outcomes at a lowest possible cost. According to some embodiments, the CNA enables identification of a specific patient as a candidate for a specific treatment, clinical trial, or drug. According to some embodiments, the CNA provides an analytic interface with connections to claims data to support health plans, hospitals and physician practices in managing doctors and other health care providers. According to some embodiments, CNAs reduce processing requirements and time for processing to make real-time monitoring efficient based on the discrete punctuated string of digits representing each nodal address and based on the reduction in permutations. This real time monitoring enables prediction of key points in time at which, for example, behavioral variance is likely to occur and interrupts treatment flow to avoid over-/under-utilization of care to prevent the behavioral variance.

Figure 5:
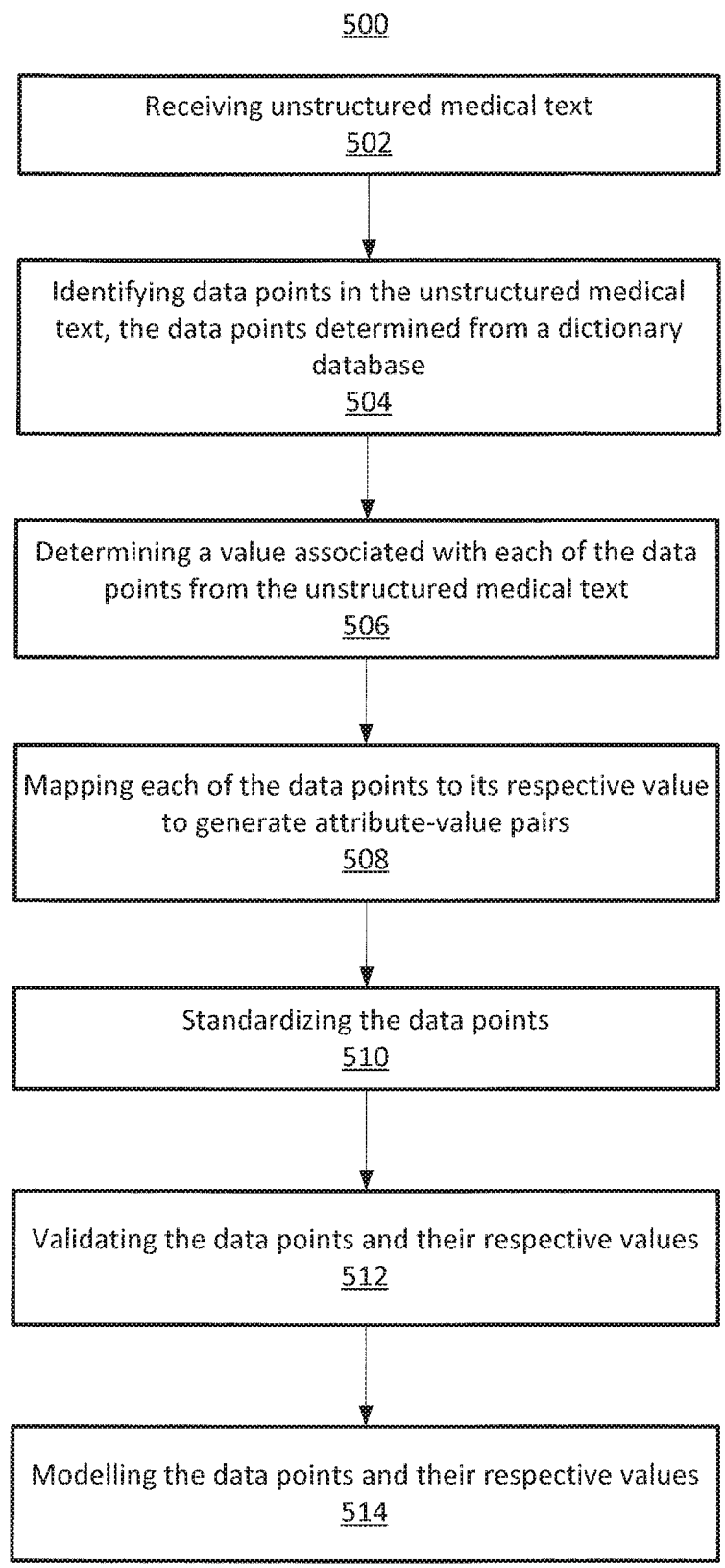
FIG. 5 illustratively depicts a flow diagram of a method for identifying and extracting prognostically significant data from unstructured text, in accordance with one embodiment.

FIG. 5 shows a flow diagram of a method 500 of operation of the extraction system 106, in accordance with one or more embodiments.

At step 502, unstructured medical text is received. The unstructured medical text may be sentences or phrases in the form of a natural language (e.g., based on grammar rules (e.g., English language grammar rules). For example, the unstructured medical text may be notations of a patient from a doctor. In one embodiment, the unstructured medical text includes unstructured oncologic text.

At step 504, data points determined from a dictionary database are identified in the unstructured medical text. For example, the unstructured medical text may be parsed to identify the data points.

In one embodiment, the dictionary database is generated (e.g., as a preprocessing step). A plurality of data points is received that are known to be diagnostically and prognostically significant. The plurality of data points may be determined from the doctor evaluating the patient, other doctors or medical experts, advisory boards, or any other suitable source. Equivalent data points of the plurality of data points are determined. The equivalent data points are data points that are synonyms of the plurality of data points or morphological variations of the plurality of data points. The plurality of data points and the equivalent data points are stored to generate the dictionary database.

At step 506, a value associated with each of the data points is determined from the unstructured medical text. The value may be syntactically or semantically dependent on its respective data points. For example, probabilistic or semantic analysis may be performed to identify a value from the unstructured medical text for each of the data points.

At step 508, each of the data points is mapped to its respective value to generate attribute-value pairs. The mapping may be store the attribute-value pairs as a list of attribute-value pairs, a collection of tuples, a table, or any other suitable data structure.

At step 510, the data points (i.e., attributes in the attribute-value pairs) are standardized. In one embodiment, each attribute is assigned or converted to a corresponding UMLS code. Other standardizations may be employed in accordance with the present principles.

At step 512, the data points and their respective values are validated to ensure integrity. For example, the data points and their respective values may be validated by identifying inconsistencies with the set of data points and values or by identifying data points having a respective value that cannot be correct.

At step 512, the data points and their respective values are modelled to provide actionable insight.

Advantageously, data points and their respective values are extracted from the unstructured medical text to provide useful information of prognostic and diagnostic significance. These data points and their respective values can be further analyzed to provide actionable insights. For example, the data points and their respective values can be employed to assign a CNA to a patient. The CNA may be represented as a discrete punctuated string of digits each representing a set of preselected variables Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the method steps described herein, including one or more of the steps of FIG. 5. Certain steps of the methods described herein, including one or more of the steps of FIG. 5, may be performed by a server or by another processor in a network-based cloud-computing system. Certain steps of the methods described herein, including one or more of the steps of FIG. 5, may be performed by a client computer in a network-based cloud computing system. The steps of the methods described herein, including one or more of the steps of FIG. 5, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method steps described herein, including one or more of the steps of FIG. 5, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 6:
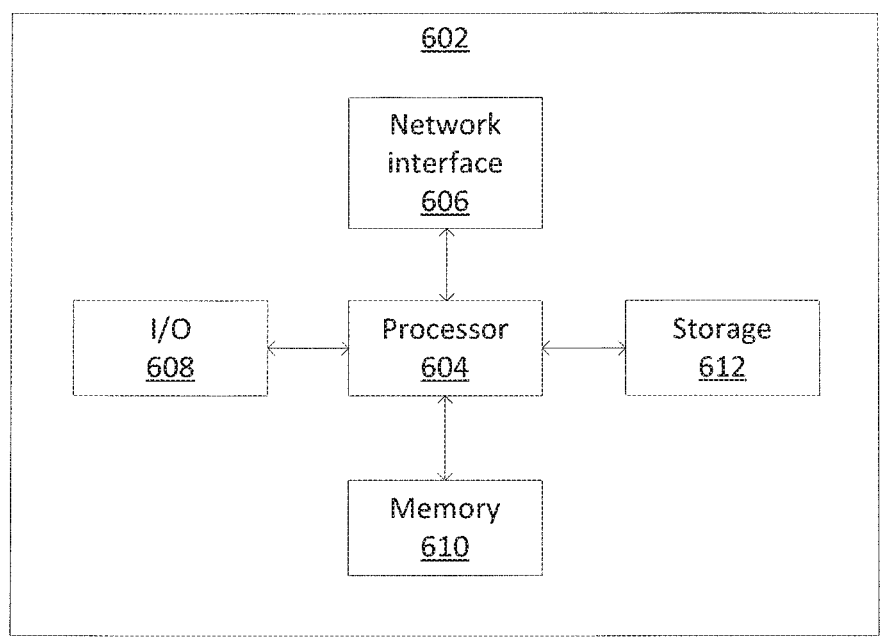
FIG. 6 shows a high-level block diagram of a computer for an extraction system, in accordance with one embodiment.

A high-level block diagram 600 of an example computer that may be used to implement systems, apparatus, and methods described herein is depicted in FIG. 6. Computer 602 includes a processor 604 operatively coupled to a data storage device 612 and a memory 610. Processor 604 controls the overall operation of computer 602 by executing computer program instructions that define such operations. The computer program instructions may be stored in data storage device 612, or other computer readable medium, and loaded into memory 610 when execution of the computer program instructions is desired. Thus, the method steps of FIG. 5 can be defined by the computer program instructions stored in memory 610 and/or data storage device 612 and controlled by processor 604 executing the computer program instructions. For example, the computer program instructions can be implemented as computer executable code programmed by one skilled in the art to perform the method steps of FIG. 5. Accordingly, by executing the computer program instructions, the processor 604 executes the method steps of FIG. 5. Computer 602 may also include one or more network interfaces 606 for communicating with other devices via a network. Computer 602 may also include one or more input/output devices 608 that enable user interaction with computer 602 (e.g., display, keyboard, mouse, speakers, buttons, etc.).

Processor 604 may include both general and special purpose microprocessors, and may be the sole processor or one of multiple processors of computer 602. Processor 604 may include one or more central processing units (CPUs), for example. Processor 604, data storage device 612, and/or memory 610 may include, be supplemented by, or incorporated in, one or more application-specific integrated circuits (ASICs) and/or one or more field programmable gate arrays (FPGAs).

Data storage device 612 and memory 610 each include a tangible non-transitory computer readable storage medium. Data storage device 612, and memory 610, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 608 may include peripherals, such as a printer, scanner, display screen, etc. For example, input/output devices 608 may include a display device such as a cathode ray tube (CRT) or liquid crystal display (LCD) monitor for displaying information to the user, a keyboard, and a pointing device such as a mouse or a trackball by which the user can provide input to computer 602.

Any or all of the systems and apparatus discussed herein, including computing devices 102 of FIG. 1 and components of extraction system 106 of FIGS. 1 and 2, may be implemented using one or more computers such as computer 602.

One skilled in the art will recognize that an implementation of an actual computer or computer system may have other structures and may contain other components as well, and that FIG. 6 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for selectively extracting objective oncologic data of diagnostic or prognostic significance from subjective unstructured medical text including text in a natural language and for providing information for treatment of one or more patients, the method comprising:
   (A) receiving input comprising unstructured medical text including unstructured oncologic text regarding one or more patients, the unstructured oncologic text including doctor's notes and impressions recorded in the patient's medical records regarding an in person visit with the patient from a doctor treating the patient;
   (B) processing the unstructured medical text to generate attribute-value pairs for each of the one or more patients, the processing including:
      (i) selectively identifying, in the unstructured medical text, data points and equivalents of the data points that are significant for diagnosis and prognosis in the context of oncology as extracted data points significant for diagnosis and prognosis in the context of oncology, the identification based on a database comprising a dictionary of medical knowledge that includes data points significant to diagnosis and prognosis in the context of oncology for more than one type of cancer and equivalents of the data points;
      (ii) selectively extracting from the unstructured medical text all facts of known importance associated with words or phrases in the unstructured medical text that are syntactically or semantically dependent on or related to the extracted data points significant for diagnosis and prognosis in the context of oncology;
      (iii) associating the extracted data points with the words or phrases in the unstructured medical text that are syntactically or semantically dependent on, or related to, the extracted data points;
      (iv) mapping each extracted data point (attribute) with its syntactically or semantically dependent word or phrase (value) in (iii) to generate attribute-value pairs; and
      (v) for at least some of the attribute-value pairs, standardizing the attribute in the attribute-value pair according to a code that represents the attribute;
   (C) validating the standardized attribute-value pairs to ensure oncologic integrity for each of the one or more patients, the validation including:
      (i) identifying inconsistencies between different standardized attribute-value pairs comprising inconsistencies based on cancer type and patient performance; and
      (ii) identifying incorrect values by identifying values that lay outside a possible range for a corresponding attribute or that are not in a possible set of values for the corresponding attribute;
   (D) grouping the standardized and validated attribute-value pairs into one or more lists of one or more grouped attribute-value pairs based on an oncologic model for each of the one or more patients, including identifying a progression or progressions of the cancer for the patient based on the oncologic model, defining one or more progression time periods based on the identified progression or progressions, and grouping attribute-value pairs by associated progression time period, each progression time period corresponding to a different stage in the patient's journey through cancer based on the oncologic model;
   (E) for each of the one or more patients, assigning the patient to a nodal address that matches attributes of the patient based on at least one of the one or more lists of one or more grouped attribute-value pairs corresponding to a current progression time period in the patient's journey through cancer, the nodal address representing values of a particular group of classification variables for the current progression time period wherein the nodal address is associated with one or more treatment plans; and (F) for at least one of the one or more patients, delivering, via a network to a user on a remote computer, actionable information regarding the one or more treatment plans to a user based on the nodal address to which the patient is assigned.

2. The method as recited in claim 1, wherein each nodal address represents a set of preselected variables effective to partition sorted personal health information for each patient in a patient population using a sorting filter to provide a sorted set of personal health information comprising a clinically relevant data set of the preselected variables for that population, to identify patients satisfying each clinically relevant parameter in the patient population, and to assign like patients in the patient population with the same set of clinically relevant data set of the preselected variables to the same nodal address;

wherein each nodal address reduces trillions of possible permutations to a reduced number of clinically meaningful permutations based on the particular group of classification variables represented in the nodal address; and wherein the method further comprises generating a unique nodal address for each combination of diagnostically and prognostically significant data points that occurs in the one or more patients at the current progression time period in the patient's journey through cancer.

3. The method as recited in claim 1, wherein
(a) at least some of the unstructured medical text in the input is in the form of an image of textual information; or
(b) at least some of the unstructured medical text is a notation from a doctor in the form of sentences or phrases based on grammar rules relating to an oncologic condition of a patient evaluated by the doctor; or
(c) the unstructured oncologic text includes one or more of demographic parameters, a simple indicator, a numerically based parameter, a standards based parameter, dates of service, medical history, medicines, diagnoses, allergies, immunization status, lab tests results, vital signs, and personal statistics.

4. The method as recited in claim 1, wherein the equivalents of the data points in the dictionary of medical knowledge comprise synonyms and morphological variations of the data points.

5. The method as recited in claim 1, wherein the code that represents each attribute comprises a unified medical language system (UMLS) code.

6. The method as recited in claim 1, wherein the delivering actionable information regarding the one or more treatment plans to the user is on a per patient basis, a per event basis, or both.

7. The method as recited in claim 6, wherein the delivering actionable information regarding the one or more treatment plans to the user on a per event basis comprises delivering actionable information regarding the one or more treatment plans based on a new diagnosis, progression of the disease, or a change in an intended clinical outcome.

8. The method as recited in claim 7, wherein a measure of the intended clinical outcome comprises one or more of overall survival (OS), progression free survival (PFS), response metrics, quality of life metrics, incidence of drug toxicity, severity of drug toxicity, delivered dose intensity, drugs received, drug interval, drug duration, cost of care, or death.

9. The method of claim 1, further comprising, prior to step (B):
receiving one or more lists of data points known to be diagnostically and prognostically significant;
determining equivalent data points to the data points known to be diagnostically and prognostically significant in the context of oncology; and
storing the identified data points known to be diagnostically and prognostically significant and the equivalent data points in the dictionary of medical knowledge.

10. The method of claim 1, wherein each list of grouped attribute-value pairs comprises two or more of: a date or relative time point, a disease, a diagnosis, a tumor type, histology, a stage, and a staging methodology.

11. The method of claim 10, wherein each list of grouped attribute value-pairs comprises a date, relative time point, or range of time associated with all of the attribute-value pairs in the group.

12. The method of claim 1, wherein each list of grouped attribute-value pairs includes one or more attribute-value pairs that provide context for another attribute-value pair in the list.

13. The method of claim 1, wherein identifying inconsistencies between standardized attribute-data pairs is based, at least in part, on data regarding a cancer type extracted from the unstructured medical text.

14. The method of claim 1, wherein identifying inconsistencies between different standardized attribute-value pairs using the oncologic model includes identifying inconsistencies between different standardized attribute-value pairs in a same list.

15. The method according to claim 2, wherein each nodal address comprises a discrete punctuated string of digits comprising a prefix, a middle, and a suffix that represents the set of preselected variables effective to partition sorted personal health information for a patient in the patient population.

16. The method according to claim 1, further comprising:
receiving second input comprising updated unstructured medical oncologic text regarding at least one of the one or more patients; and
for each of the at least one of the one or more patients:
processing the updated unstructured medical oncologic text regarding the patient to generate updated attribute-value pairs;
validating the updated attribute-value pairs to ensure oncologic integrity;
grouping the attribute-value pairs and updated attribute value-pairs for the patient into one or more lists of grouped attribute-value pairs based on the oncologic model;
determining if the nodal address of the patient changes based on at least one of the one or more lists, and where the nodal address of the patient changes, assigning the patient to an updated nodal address, wherein the nodal address is associated with one or more updated treatment plans; and
where the nodal address of the patient changes, delivering updated actionable information regarding the one or more updated treatment plans to a user based on the updated nodal address to which the patient is assigned.

17. A non-transitory computer readable storage medium storing computer program instructions for selectively extracting objective oncologic data of diagnostic or prognostic significance from unstructured medical text including text in a natural language and for providing information for treatment of one or more patients, which, when executed on one or more processors, cause the one or more processors to perform operations comprising:
- (A) receiving input comprising unstructured medical text including unstructured oncologic text regarding one or more patients, the unstructured oncologic text including doctor's notes and impressions recorded in the patient's medical records regarding an in person visit with the patient from a doctor treating the patient;
- (B) processing the unstructured medical text to generate attribute-value pairs for each of the one or more patients, the processing including:
  - (i) selectively identifying in the unstructured medical text data points and equivalents of the data points that are significant for diagnosis and prognosis in the context of oncology as extracted data points significant for diagnosis and prognosis in the context of oncology, the identification based on a database comprising a dictionary of medical knowledge that identifies data points significant to diagnosis and prognosis in the context of oncology for more than one type of cancer and equivalents of the data points;
  - (ii) selectively extracting from the unstructured medical text all facts of known importance associated with words or phrases in the unstructured medical text that are syntactically or semantically dependent on or related to the extracted data points significant for diagnosis and prognosis in the context of oncology;
  - (iii) associating the extracted data points with the words or phrases in the unstructured medical text that are syntactically or semantically dependent on, or related to, the extracted data points;
  - (iv) mapping each extracted data point (attribute) with its syntactically or semantically dependent word or phrase (value) in (iii) to generate attribute value pairs; and
  - (v) for at least some of the attribute-value pairs, standardizing the attribute in the attribute-value pair according to a code that represents the attribute;
- (C) validating the standardized attribute-value pairs to ensure oncologic integrity for each of the one or more patients, the validation including:
  - (i) identifying inconsistencies between different standardized attribute-value pairs comprising inconsistencies based on cancer type and patient performance; and
  - (ii) identifying incorrect values by identifying values that lay outside a possible range for a corresponding attribute or that are not in a possible set of values for the corresponding attribute;
- (D) grouping the standardized and validated attribute-value pairs into one or more lists of one or more grouped attribute-value pairs based on an oncologic model for each of the one or more patients, including identifying a progression or progressions of the cancer for the patient based on the oncologic model, defining one or more progression time period based on the identified progression or progressions, and grouping attribute-value pairs corresponding to by associated progression time period, each progression time period corresponding to a different stage in the patient's journey through cancer based on the oncologic model;
- (E) for each of the one or more patients, assigning the patient to a nodal address that matches attributes of the patient based on at least one of the one or more lists of one or more grouped attribute-value pairs corresponding to a current progression time period in the patient's journey through cancer, the nodal address representing values of a particular group of classification variables for the current progression time period wherein the nodal address is associated with one or more treatment plans; and
- (F) for at least one of the one or more patients, delivering, via a network to a user on a remote computer, actionable information regarding the one or more treatment plans to a user based on the nodal address to which the patient is assigned.

18. The non-transitory computer readable storage medium as recited in claim 17, wherein each nodal address represents a set of preselected variables effective to partition sorted personal health information for each patient in a patient population using a sorting filter to provide a sorted set of personal health information comprising a clinically relevant data set of the preselected variables for that population, to identify patients satisfying each clinically relevant parameter in the patient population, and to assign like patients in the patient population with the same set of clinically relevant data set of the preselected variables to the same nodal address;
- wherein each nodal address reduces trillions of possible permutations to a reduced number of clinically meaningful permutations based on the particular group of classification variables represented in the nodal address; and
- wherein the operations further comprise generating a unique nodal address for each combination of diagnostically and prognostically significant data points that occurs in the one or more patients at the current progression time period in the patient's journey through cancer.

19. The non-transitory computer readable storage medium as recited in claim 17, wherein
- (a) at least some of the unstructured medical text in the input is in the form of an image of textual information; or
- (b) at least some of the unstructured medical text is a notation from a doctor in the form of sentences or phrases based on grammar rules relating to an oncologic condition of a patient evaluated by the doctor; or
- (c) the unstructured oncologic text includes one or more of demographic parameters, a simple indicator, a numerically based parameter, a standards based parameter, dates of service, medical history, medicines, diagnoses, allergies, immunization status, lab tests results, vital signs, personal statistics.

20. The non-transitory computer readable storage medium as recited in claim 17, wherein the equivalents of the data points in the dictionary of medical knowledge comprise synonyms and morphological variations of the data points.

21. The non-transitory computer readable storage medium as recited in claim 17, wherein the code that represents each attribute comprises a unified medical language system (UMLS) code.

22. The non-transitory computer readable storage medium as recited in claim 17, wherein the delivering actionable information regarding the one or more treatment plans to the user is on a per patient basis, a per event basis, or both.

23. The non-transitory computer readable storage medium as recited in claim 22, wherein the delivering actionable information regarding the one or more treatment plans to the user on a per event basis comprises delivering actionable information regarding the one or more treatment plans based on a new diagnosis, progression of the disease, or a change in an intended clinical outcome.

24. The non-transitory computer readable storage medium as recited in claim 23, wherein a measure of the intended clinical outcome comprises one or more of overall survival (OS), progression free survival (PFS), response metrics, quality of life metrics, incidence of drug toxicity, severity of drug toxicity, delivered dose intensity, drugs received, drug interval, drug duration, cost of care, or death.

25. A system for selectively extracting objective oncologic data of diagnostic or prognostic significance from unstructured medical text including text in a natural language and for providing information for treatment of one or more patients, comprising:
    a first database comprising a dictionary of medical knowledge that identifies data points as significant to diagnosis and prognosis in the context of oncology for more than one type of cancer and equivalents of the data points;
    a second database comprising personal health information data for a population of human subjects;
    wherein the first and second database are communicatively linked using a common patient identifier and through the use of database access using the common patient identifier; and
    an extraction system comprising:
        a computer server including one or more processors comprising a clinical outcome tracking and analysis module communicatively linked to the first database, the second database, and the network; and
        a memory to store computer program instructions, the computer program instructions when executed on the one or more processors cause the one or more processors to perform operations comprising:
        (A) receiving input comprising unstructured medical text including unstructured oncologic text regarding one or more patients, the unstructured oncologic text including doctor's notes and impressions recorded in the patient's medical records regarding an in person visit with the patient from a doctor treating the patient;
        (B) processing the unstructured medical text to generate attribute-value pairs for each of the one or more patients, the processing including:
            (i) selectively identifying in the unstructured medical text data points and equivalents of the data points that are significant for diagnosis and prognosis in the context of oncology as extracted data points significant for diagnosis and prognosis in the context of oncology, the identification based on the dictionary of medical knowledge of the first database;
            (ii) selectively extracting from the unstructured medical text all facts of known importance associated with words or phrases in the unstructured medical text that are syntactically or semantically dependent on or related to the extracted data points significant for diagnosis and prognosis in the context of oncology;
            (iii) associating each extracted data point with the words or phrases in unstructured medical text that are syntactically or semantically dependent on, or related to, the extracted data point;
            (iv) mapping each extracted data point (attribute) with its syntactically or semantically dependent word or phrase (value) in (iii) to generate attribute value pairs; and
            (v) for at least some of the attribute-value pairs, standardizing the attribute in the attribute-value pair according to a code that represents the attribute;
        (C) validating the standardized attribute-value pairs to ensure oncologic integrity for each of the one or more patients, the validation including:
            (i) identifying inconsistencies between different standardized attribute-value pairs comprising inconsistencies based on cancer type and patient performance; and
            (ii) identifying incorrect values by identifying values that lay outside a possible range for a corresponding attribute or that are not in a possible set of values for the corresponding attribute;
        (D) grouping the standardized and validated attribute-value pairs into one or more lists of one or more grouped attribute-value pairs based on an oncologic model for each of the one or more patients, including identifying a progression or progressions of the cancer for the patient based on the oncologic model, defining one or more progression time periods based on the identified progression or progressions, and grouping attribute-value pairs by associated progression time period, each progression time period corresponding to a different stage in the patient's journey through cancer based on the oncologic model;
        (E) for each of the one or more patients, assigning the patient to a nodal address that matches attributes of the patient based on at least one of the one or more lists of one or more grouped attribute-value pairs corresponding to a current progression time period in the patient's journey through cancer, the nodal address representing values of a particular group of classification variables for the current time period wherein the nodal address is associated with one or more treatment plans; and
        (F) for at least one of the one or more patients, delivering, via a network to a user on a remote computer, actionable information regarding the one or more treatment plans to a user based on the nodal address to which the patient is assigned.

26. The system as recited in claim 25, wherein each nodal address represents a set of preselected variables effective to partition sorted personal health information for each patient in a patient population using a sorting filter to provide a sorted set of personal health information comprising a clinically relevant data set of the preselected variables for that population, to identify patients satisfying each clinically relevant parameter in the patient population, and to assign like patients in the patient population with the same set of clinically relevant data set of the preselected variables to the same nodal address;
    wherein each nodal address reduces trillions of possible permutations to a reduced number of clinically meaningful permutations based on the particular group of classification variables represented in the nodal address; and
    wherein the operations further comprise generating a unique nodal address for each combination of diagnostically and prognostically significant data points that occurs in the one or more patients at the current progression time period in the patient's journey through cancer.

27. The system as recited in claim 25, wherein
(a) at least some of the unstructured medical text is in the form of an image of textual information; or (b) at least some of the unstructured medical text is a notation from a doctor in the form of sentences or phrases based on grammar rules relating to an oncologic condition of a patient evaluated by the doctor; or
(c) the unstructured oncologic text includes one or more of demographic parameters, a simple indicator, a numerically based parameter, a standards based parameter, dates of service, medical history, medicines, diagnoses, allergies, immunization status, lab tests results, vital signs, personal statistics; or
(d) the equivalents of the data points comprise synonyms and morphological variations of the data points; or
(e) the code that represents each attribute comprises a unified medical language system (UMLS) code; or
(f) the delivering actionable information regarding the one or more treatment plans to the user is on a per patient basis, a per event basis, or both.

28. The system as recited in claim 27, wherein the delivering actionable information regarding the one or more treatment plans to the user on a per event basis comprises delivering actionable information regarding the one or more treatment plans to the user per diagnosis, per treatment, per progression, or per clinical outcome.

29. The system as recited in claim 28, wherein a measure of the clinical outcome comprises one or more of overall survival (OS), progression free survival (PFS), response metrics, quality of life metrics, incidence of drug toxicity, severity of drug toxicity, delivered dose intensity, drugs received, drug interval, drug duration, cost of care, or death.

\* \* \* \* \*